(12) United States Patent
Dumont et al.

(10) Patent No.: US 9,259,752 B2
(45) Date of Patent: Feb. 16, 2016

(54) FLUID PRODUCT DISPENSING BOTTLE

(71) Applicants: Pierre Dumont, Dargnies (FR); Mohamed Elmeguenni, Mers les Bains (FR); Jacky Lasnier, Sainte Marguerite sur Duclair (FR); Jean-Luc Octau, Intraville (FR); Emmanuel Mauduit, Abbeville (FR)

(72) Inventors: Pierre Dumont, Dargnies (FR); Mohamed Elmeguenni, Mers les Bains (FR); Jacky Lasnier, Sainte Marguerite sur Duclair (FR); Jean-Luc Octau, Intraville (FR); Emmanuel Mauduit, Abbeville (FR)

(73) Assignee: ALBEA LE TREPORT S.A.S. (FR)

( * ) Notice: Subject to any disclaimer, the term of this patent is extended or adjusted under 35 U.S.C. 154(b) by 344 days.

(21) Appl. No.: 14/018,126

(22) Filed: Sep. 4, 2013

(65) Prior Publication Data

US 2014/0060695 A1 Mar. 6, 2014

(30) Foreign Application Priority Data

Sep. 4, 2012 (FR) ..................................... 12 58251

(51) Int. Cl.
*B05B 11/00* (2006.01)
*B65D 1/06* (2006.01)
*A61M 11/08* (2006.01)
(Continued)

(52) U.S. Cl.
CPC .......... *B05B 11/3042* (2013.01); *B05B 11/0056* (2013.01); *B05B 11/306* (2013.01); *B65D 1/06* (2013.01); *A45D 2200/056* (2013.01); *A61M 11/08* (2013.01); *A61M 15/009* (2013.01); *A61M 15/08* (2013.01); *B05B 11/0016* (2013.01); *B05B 11/3026* (2013.01); *B05B 11/3047* (2013.01)

(58) Field of Classification Search
CPC ...... B65D 1/06; B05B 11/30; B05B 11/3042; B05B 11/0016; B05B 11/0056
USPC .......................................... 141/65, 113; 215/2
See application file for complete search history.

(56) References Cited

U.S. PATENT DOCUMENTS 3,718,165 A * 2/1973 Grothoff ................... B65B 3/04
137/583
5,791,527 A * 8/1998 Giuffredi ............ B05B 11/0056
141/113

(Continued)

FOREIGN PATENT DOCUMENTS

EP 0657223 A1 6/1995
EP 2441344 A1 4/2012
(Continued)

OTHER PUBLICATIONS

French Search Report Application No. FR 1258251 Issued: Apr. 18, 2013 6 pages.

*Primary Examiner* — Timothy L Maust
(74) *Attorney, Agent, or Firm* — St Onge Steward Johston and Reens LLC

(57) ABSTRACT

A bottle for dispensing a fluid product including a body in which a container intended for packaging the product is formed, the bottle also including an extraction device equipped with a pushbutton reversibly movable over a stroke for actuation of the device between a resting position and a depressed position in which the dispensing orifice is in communication with the container via the device, the body being equipped with a valve for filling the container by suction of the product contained in a product source, an upper wall being integrated in the body by way of a sealed connection that can be destroyed manually, the extraction device being mounted in the body with the pushbutton held in the depressed position on the upper wall so as to place the connection in communication with the container.

14 Claims, 4 Drawing Sheets

(51) Int. Cl.
*A61M 15/00* (2006.01)
*A61M 15/08* (2006.01)

(56) References Cited

U.S. PATENT DOCUMENTS 7,665,635 B2 * 2/2010 Ramet ................. B05B 11/0056
 141/113
8,662,116 B2 * 3/2014 Dumont ............. B05B 11/0056
 141/113
8,695,896 B2 * 4/2014 Tu ....................... B05B 11/0056
 141/113
9,138,764 B2 * 9/2015 Farrar ................. B05B 11/0043
9,146,144 B2 * 9/2015 Hui ....................... G01F 11/028

FOREIGN PATENT DOCUMENTS

FR 2854131 A1 10/2004
WO 03066235 A1 8/2003
WO 2006129044 A2 12/2006

* cited by examiner

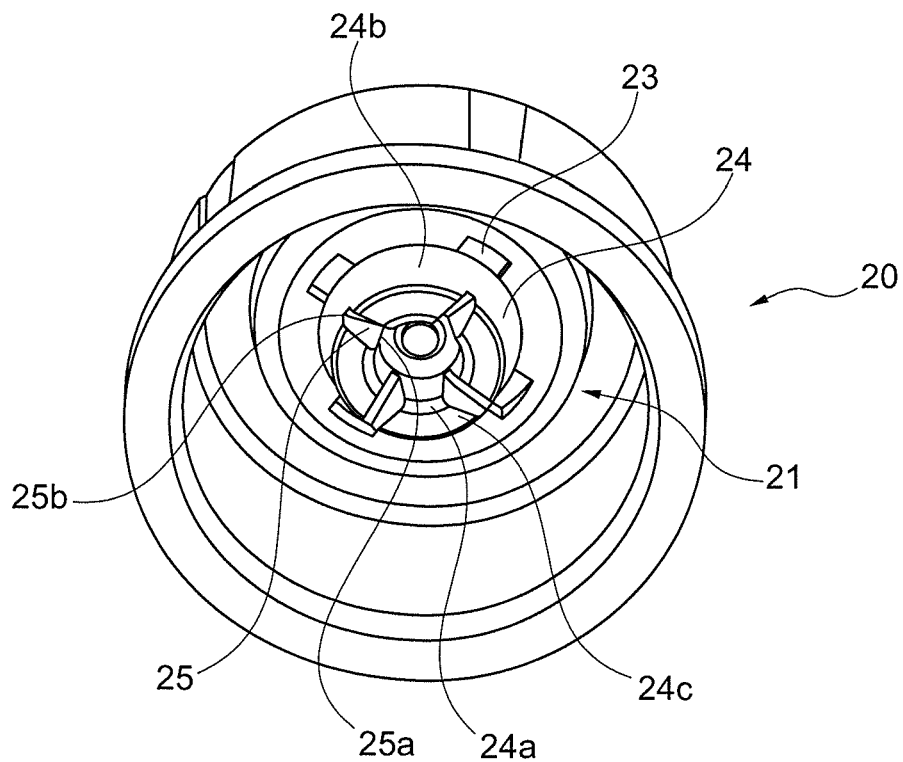
Fig. 4
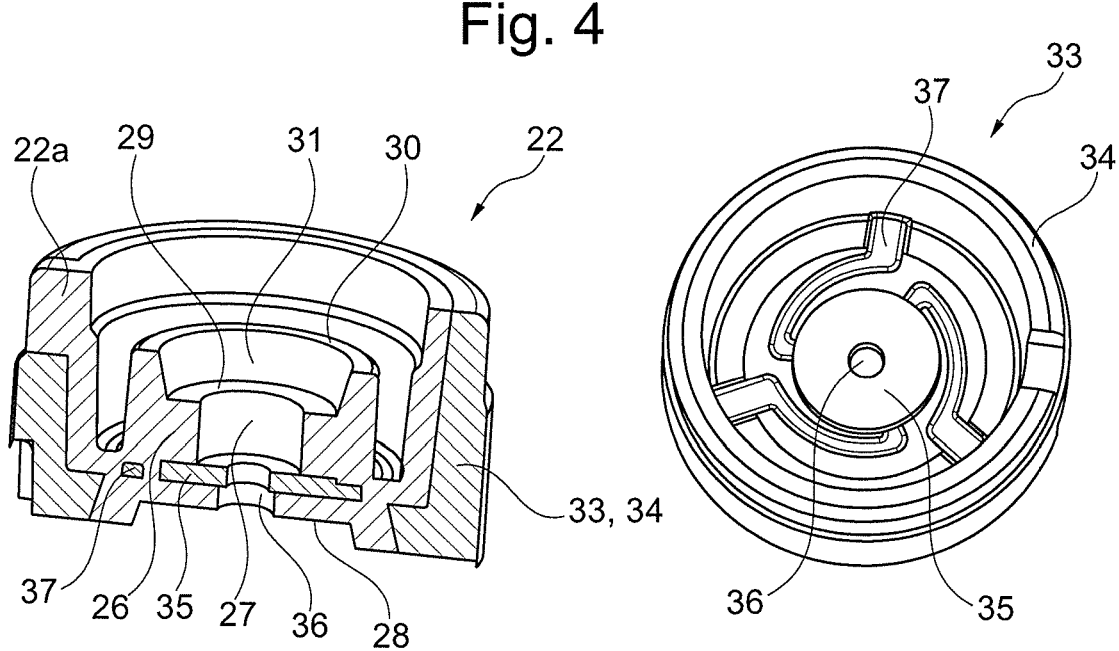
Fig. 5
Fig. 6

FLUID PRODUCT DISPENSING BOTTLE

FIELD OF THE INVENTION

The invention relates to a bottle for dispensing a fluid product, in particular a liquid, for example, a cosmetic care, makeup or fragrance product, or a pharmaceutical product.

BACKGROUND OF THE INVENTION

The dispensing bottle comprises a body in which a container for packaging the product is formed, as well as a device for extracting the packaged product, which is mounted in a sealed manner in said body. In particular, the extraction device can comprise a manually actuated pump that is supplied with the packaged product, said pump being arranged so as to dispense the pressurized product, for example in the form of an aerosol.

To do this, the extraction device is equipped with a pushbutton that is equipped with a product dispensing orifice, said pushbutton being reversibly movable over a stroke for actuation of said device between a resting position and a depressed position in which the dispensing orifice is in communication with the container by means of said device.

In the application example, the bottles according to the invention enable product samples to be dispensed, in particular for a product volume packaged in the container of between 1 and 10 ml. In particular, the samples thus dispensed can enable a client to test the product, the bottles then being qualified as test sample bottles. Alternatively, the bottles can be "for bags" in that they enable a reduced volume of product to be carried easily, by contrast with bottles containing a larger volume, which are generally heavy and bulky because they are large.

In these applications, for example for logistical reasons, practicality or environmental recycling reasons, it may be desirable to be capable of refilling the container with product from a source of said product. Indeed, it is impractical for a user to fill the container using a small funnel, and non-environmentally friendly to throw away an empty bottle in order to replace it with a full refill container.

Dispensing bottles have already been offered for sale, in which the body is equipped with a valve for filling the container that is arranged so as to enable a product source to communicate with said container. In particular, the valve may be opened by pressing on the outlet tube of the pump of a source bottle, which is suitable for being actuated numerous times in order to fill the container by injection of the source product, which is a non-intuitive action for the user.

Document FR-2 854 131 relates to the draining of a container by means of a dispensing pump without taking air into the packaging container to compensate for the product volume dispensed so as to create an air depression in said container, said depression enabling said container to be filled by suction of the source product.

Document EP-2 441 344 proposes dispensing bottles of which the container is empty of product and has an air depression that is arranged so as to be capable of subsequently performing the initial filling of the container with product by placing, in sealed communication, a product source with said container by means of a valve so that said depression induces the filling of said container by suction of the product contained in said source.

However, in the filling-by-suction solutions, there is the problem of preservation over time of the air depression in the container. Indeed, the extraction devices are never perfectly impervious to micro-leakages of air because they comprise numerous areas sealed by tightening and are made of plastic or elastomeric materials that, over time, are found to be slightly porous to air.

SUMMARY OF THE INVENTION

The invention is intended to improve on the prior art by proposing, in particular, a dispensing bottle in which an air depression in the container can be preserved for a prolonged period, in particular during storage of the bottle before its initial filling, so as to make the capacity for filling by suction of said container reliable by placing a product source in sealed communication with said container.

To this effect, the invention proposes a bottle for dispensing a fluid product comprising a body in which a container intended for packaging said product is formed, said bottle also comprising a device for extracting said packaged product, which is mounted in a sealed manner in said body, said extraction device being equipped with a pushbutton that is equipped with an orifice for dispensing said product, said pushbutton being reversibly movable over a stroke for actuation of said device between a resting position and a depressed position in which the dispensing orifice is in communication with the container by means of said device, said body being equipped with a valve for filling said container that is arranged so as to enable a product source to be placed in communication with said container, the container having an air depression that is arranged so as to be capable of filling the container with product by suction of the product contained in said source, an upper wall being integrated with the body by way of sealed connection means that can be destroyed manually, said extraction device being mounted in said body with the pushbutton held in the depressed position on said upper wall so as to place said connection means in communication with said container.

BRIEF DESCRIPTION OF THE DRAWINGS

Other objectives and advantages of the invention will appear in the following description, provided with reference to the appended figures, wherein:

FIGS. 4 to 6 are views of components of the valve for filling the bottle of FIG. 1, respectively showing the cap from the bottom perspective (FIG. 4), the deformable valve in a longitudinal cross-section (FIG. 5) and the deformable valve reinforcement from the top perspective (FIG. 6).

DETAILED DESCRIPTION OF THE INVENTION

Figures 1A, 1B, 1C, 1D:
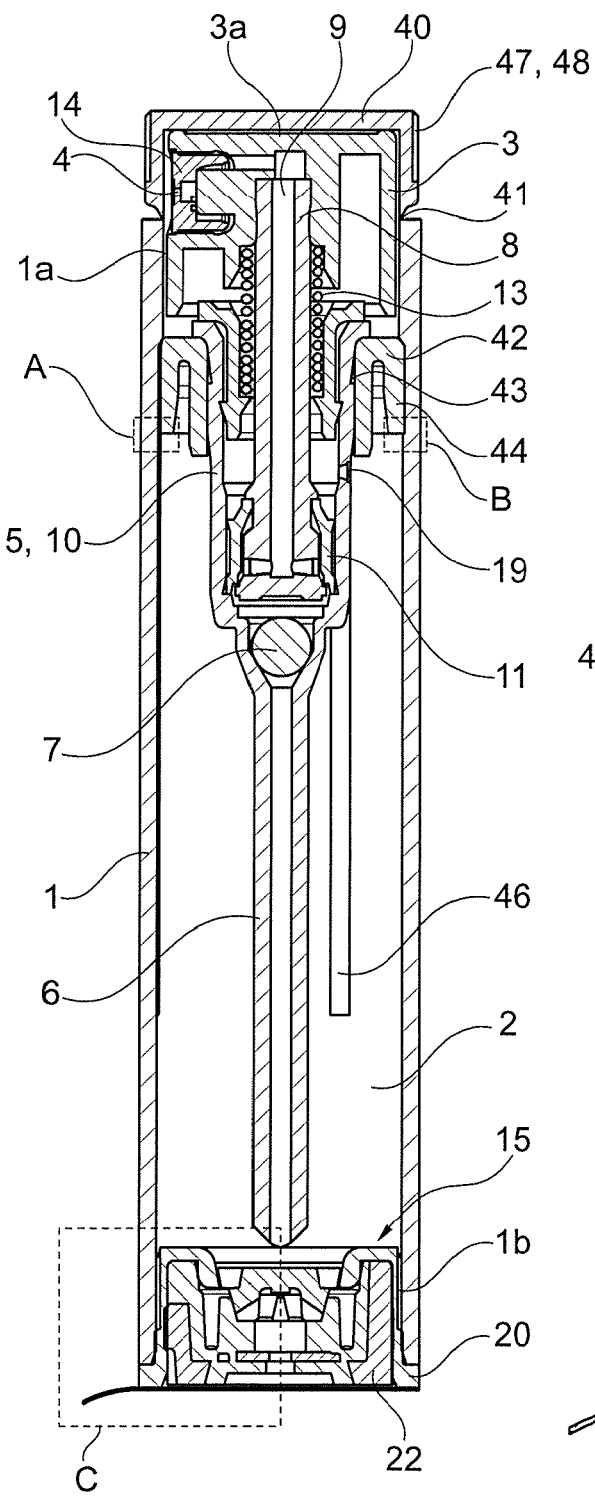
FIG. 1A is a longitudinal cross-section view of a dispensing bottle according to the invention that is shown in the storage state, FIGS. 1B to 1D being enlarged views of areas A, B and C, respectively, of FIG. 1A.

In the description, the terms of positioning in space refer to the position of the bottle shown in the figures.

In relation to the figures, a bottle intended to contain a fluid product to be dispensed will be described below. In specific examples, the product can be liquid, in particular a cosmetic care, makeup or fragrance product, or a pharmaceutical product.

The bottle comprises a body 1 in which a container 2 for packaging the product is formed. According to a particular application, the container 2 can have a capacity of between 1 and 10 ml so as to enable product samples to be dispensed.

In the embodiments shown, the body 1 is rigid, in particular having a rigidity sufficient for the volume of the container 2 to remain substantially constant, even if the internal pressure varies. The body 1 can be one-piece, for example, produced by injection-blowing or extrusion-blowing, or made of a plurality of parts injected then assembled, for example by ultrasound welding, or by laser, or by rotary friction, made of rigid plastic material, metal, for example aluminium, or glass.

The bottle comprises a device for extracting the packaged product that is mounted in a sealed manner in the body 1. In particular, the extraction device is equipped with a pushbutton 3, which is equipped with an orifice 4 for dispensing said product, said pushbutton being reversibly movable over a stroke for actuation of said device between a resting position and a depressed position in which the dispensing orifice 4 is in communication with the container 2 by means of said device.

In the embodiment shown, the extraction device comprises a dispensing pump 5 manually actuated by means of a pushbutton 3, which is supplied with the pressurized product to be dispensed.

The pump 5 comprises packaged product supply means which, in the figures, comprise a plunger tube 6 arranged in the container 2, said tube being equipped with an inlet valve 7 for the product in the pump 5. The pushbutton 3 is mounted on the spray nozzle 8 of the pump 3, placing the dispensing orifice 4 in communication with an outlet channel 9 of said spray nozzle.

The pump 5 also comprises a casing 10 in which a piston 11 mounted around the spray nozzle 8 is arranged so as to define a dosing chamber 12 in said casing, said spray nozzle being reversibly movable over a dispensing stroke—suction stroke, respectively—in which the piston 11 opens—closes, respectively—the communication between the outlet channel 9 and the dosing chamber 12.

The pushbutton 3 comprises an upper area 3a enabling the user to exert finger pressure on said pushbutton so as to be capable of moving the spray nozzle 8 over its dispensing stroke until a depressed position of said pushbutton is reached, the return of the pushbutton 3 to the resting position on the suction stroke of the spray nozzle 8 classically being achieved by a spring 13.

In the embodiment shown, the pushbutton 3 is equipped with a spray nozzle 14 that is arranged so as to radially dispense an aerosol of the product through the dispensing orifice 4. However, the invention is not limited to one particular way of dispensing the product. In particular, particularly for a nasal spray end-piece, the pushbutton 3 can enable axial dispensing of the product and another type of extraction device can be envisaged.

The body 1 of the bottle is equipped with a valve 15 for filling the container 2, which is arranged so as to enable the establishment of communication of a product source 16 with said container. In relation to FIG. 2, the product source 16 comprises a source container on which an outlet tube 17 is arranged, the filling of the container 2 with product being performed by mounting said tube by sealed contact on the valve 15, which is arranged so as to open reversibly.

In particular, it is possible to use, as a product source 16, a feed bottle with a greater capacity, said bottle being equipped with a pump 18 of which the pushbutton is removed so as to enable the spray nozzle 17 to be arranged with sealed contact on the valve 15. Indeed, aside from the opening of the valve 15, the sealed contact causes the pump 18 to open so as to enable the filling product to pass through it.

According to another embodiment, the source container 16 is formed inside a flexible pouch that can be filled with product without air or gas for good preservation of said product. The transfer of the product into the container is then possible in all of the positions and the flexible pouch cannot be reversed from its role as source since there is no propellant gas or internal pressure, or a pushbutton for actuating any pump or valve associated with the outlet tube 17.

The tank 2 has an air depression that is arranged to be capable of performing the filling of said container with product by establishing sealed communication of the product source 16 with said container by means of the valve 15 so that said depression induces the filling of said container by suction of the product contained in said source. In particular, the air depression can be on the order of 980 hPa.

The container 2 can be empty of product and have an initial air depression that is used to perform the first filling of said container with product. The extraction device 5 can then be of the type without taking in air to enable subsequent fillings or with the intake of air to limit the use of the bottle to only one filling. In the embodiment shown, the pump 5 is a model with air intake and therefore has a vent hole 19 that is arranged to enable the product volume extracted from the container 2 to be compensated with air.

In particular, the initial air depression can be produced by establishing communication of the empty product container 2 with an air suction device. To do this, it is possible, for example, to use an air suction device that comprises a vacuum chamber in which the dispensing bottle is arranged, the sealed mounting of the extraction device 5 in the body 1 being performed after said vacuum chamber has been activated. Thus, the depression is formed in the container 2, then the extraction device 5 is mounted in a sealed manner so as to maintain said depression.

It is also possible to use an air suction device comprising a vacuum pump, said suction device being placed in sealed communication with the valve 15 in order, after sealed mounting of the extraction device 5 in the body 1, to suction the air from the container 2 through said valve.

In the embodiment shown, the valve 15 comprises a rigid cap 20 having an internal housing 21 in which a deformable valve element 22 is mounted, said cap being mounted in a sealed manner in the body 1 in order to place the internal housing 21 in communication with the container 2 by means of a downstream passage 23. Alternatively, the valve 15 can comprise a valve element capable of moving between a stable state of closing the downstream passage 23 and a stressed state of opening said downstream passage.

The internal housing 21 has a structure 24 equipped with an intermediate passage 25 formed between an upstream opening 25a and a downstream opening 25b, the deformable valve element 22 having a seat 26 that is equipped with an upstream passage 27 formed between a lower portion 28 for receiving the outlet tube 17 of the product source 16 and an upper portion 29 on which a sealing lip 30 is mounted.

In addition, the valve 15 is arranged so as to have a stable state, in which the sealing lip 30 closes the downstream opening 25b in a sealed manner, and a stressed state by axial contact of the outlet tube 17 on the lower portion 29, in which the seat 26 is compressed by axial contact of the upper portion 29 on the structure 24 enabling communication between the upstream passage 27 and the upstream opening 25a, said compression inducing a detachment of said lip so as to open the communication between the downstream opening 25b and the downstream passage 23.

Thus, the filling of the container 2 is performed by simple pressure of the outlet tube 17 so as to place said outlet tube in sealed communication with the container 2 by means of passages 27, 25, 23, the removal of said outlet tube causing the valve 15 to return to a stable state, establishing a reliable seal through it by closing the downstream opening 25b.

Advantageously, the seal is made reliable ensuring that the sealing lip 30 is connected to the seat 26 so that the axial compression—extension, respectively—of said seat between its upper 29 and lower 28 portions induces a radial detachment—pressing, respectively—of said lip on the downstream opening 25b.

In particular, the lower 28 and upper 29 portions are annular and extend radially around the upstream passage 27 by being axially spaced apart, the lip 30 also being annular and extending radially around said upper portion by being connected to it by means of a face 31 that is outwardly inclined. Thus, when the upper portion 29 is compressed on the structure 24, the inclination of the face 31 facilitates the radial detachment of the lip 30.

In addition, the air depression formed in the container 2 urges the sealed pressing of the sealing lip 30 on the downstream opening 25b so as to make the preservation over time of said depression reliable. In addition, to improve the sealing of the valve 15, prevent its contamination by foreign bodies coming from outside and form a first use indicator, said valve can be covered reversibly with a seal 32 that the user removes or tears when he or she wants to fill the container 2. In particular, the seal 32 can be welded below the cap 20, said cap itself being welded in the body 1 so as to ensure the sealed mounting of the valve 15 in said body.

Advantageously, the valve element 22 can comprise a reinforcement 33 on which an element 22a made of an elastically deformable material is associated, in particular by over-moulding in order to facilitate the assembly of the valve 15. The seat 26 is formed on the element 22a, the reinforcement 33 comprising a peripheral wall 34 for association with the cap 20 and a plate 35 arranged between the upper 29 and lower 28 portions, having an orifice 36 through which the upstream passage 27 extends.

In particular, the plate 35 extends radially and is connected to the peripheral wall 34 by at least one arm 37 enabling an elastic axial movement of said plate inside said peripheral wall. Thus, in the stable state, the arms 37 can exert a pressing force of the sealing lip 30 on the downstream opening 25b so as to ensure the reliability of the sealing conferred.

In addition, the plate 35 ensures the uniform distribution of the force exerted by the outlet tube 17 during the filling operation, regardless of the diameter and the centring of said tube.

In the embodiment shown, the structure comprises a projection 24 having a peripheral wall defined between an interior surface 24a, an exterior surface 24b and a free lower edge 24c, the intermediate passage 25 comprising at least one hollow conduit formed in said wall with the upstream opening 25a—downstream opening 25b, respectively, leading into the interior surface 24a—exterior surface 24b, respectively.

In particular, the upstream passage 25a of each conduit 25 leads into the projection of the structure 24, the upper portion 29 being arranged opposite the lower edge 24c so as to be pressed on it in the stressed state and the sealing lip 30 in the stable state is in sealed contact on the exterior surface 24b.

In relation to FIG. 4, the intermediate passage comprises four conduits 25 spaced angularly apart by around 90°, said conduits leading into the lower edge 24c of the projection 24. In addition, the conduits 25 are inclined downward between their upstream opening 25a and downstream opening 25b, said downstream opening being closed by the base of the face 31 so as to ensure the reliability of the sealing conferred. In addition, the downstream passage 23 comprises four orifices that are arranged opposite a conduit 25, respectively.

Figures 2A, 2B:
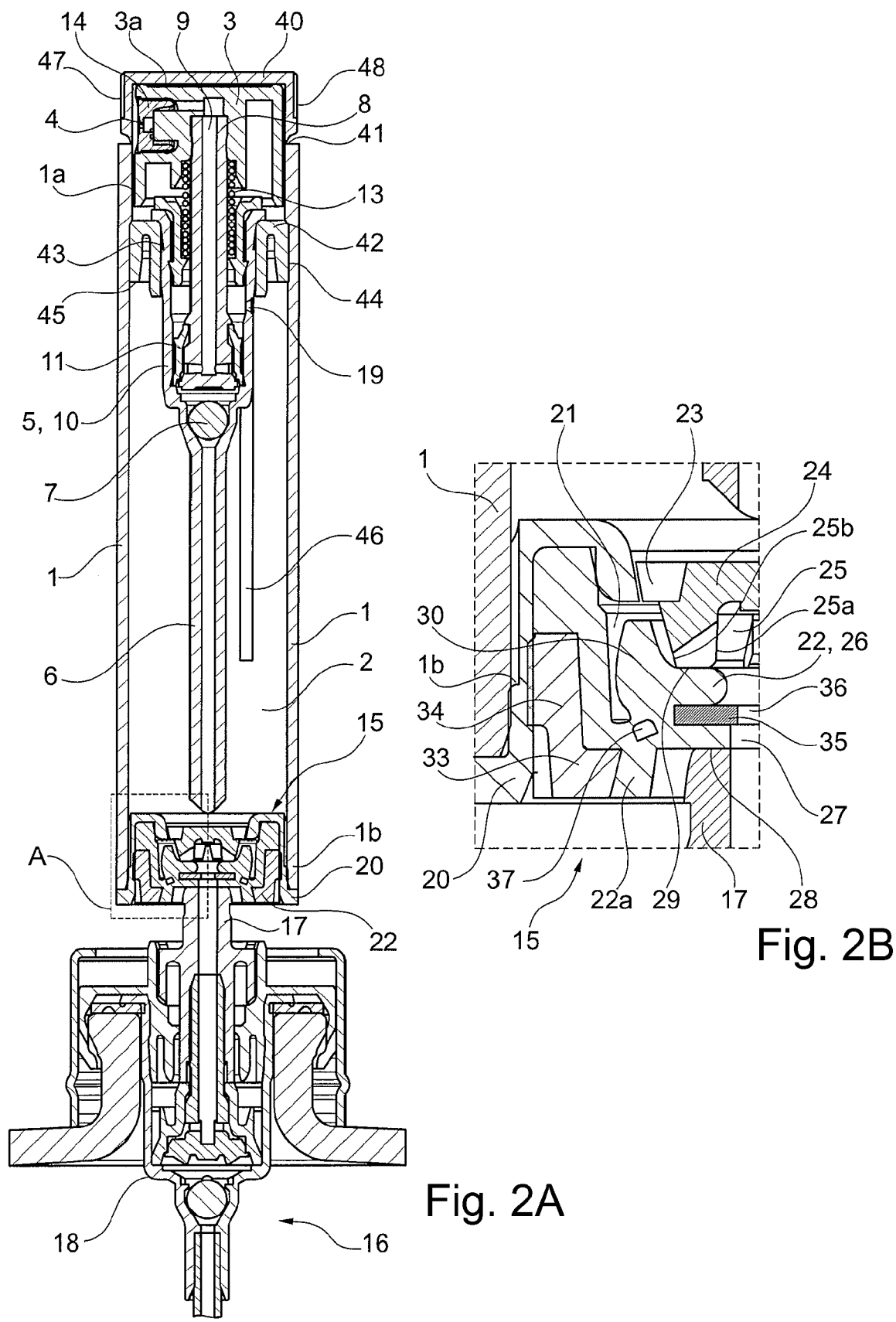
FIG. 2A is a longitudinal cross-section view of the bottle of FIG. 1A showing the filling of the container by means of a product source, FIG. 2B being an enlarged view of area A of FIG. 2A.

In relation to FIGS. 1 and 2, an upper wall 40 is integrated with the body 1 by way of sealed connection means 41, which can be destroyed manually, the extraction device 5 being mounted in said body with the pushbutton 3 held in the depressed position on said upper wall so as to place said connection means in communication with the container 2. Advantageously, the depressed position is maintained by placing the upper area 3a in axial bearing below the upper wall 40.

Thus, during storage of the bottle, the sealing of the air depression of the container 2 is not achieved at the level of the extraction device 5, which is kept in the open position, but by the integration of the upper wall 40 with the body 1, said integration being capable of being easily arranged so as to preserve said air depression over time, in particular without requiring any modification of the extraction device 5.

Figure 3:
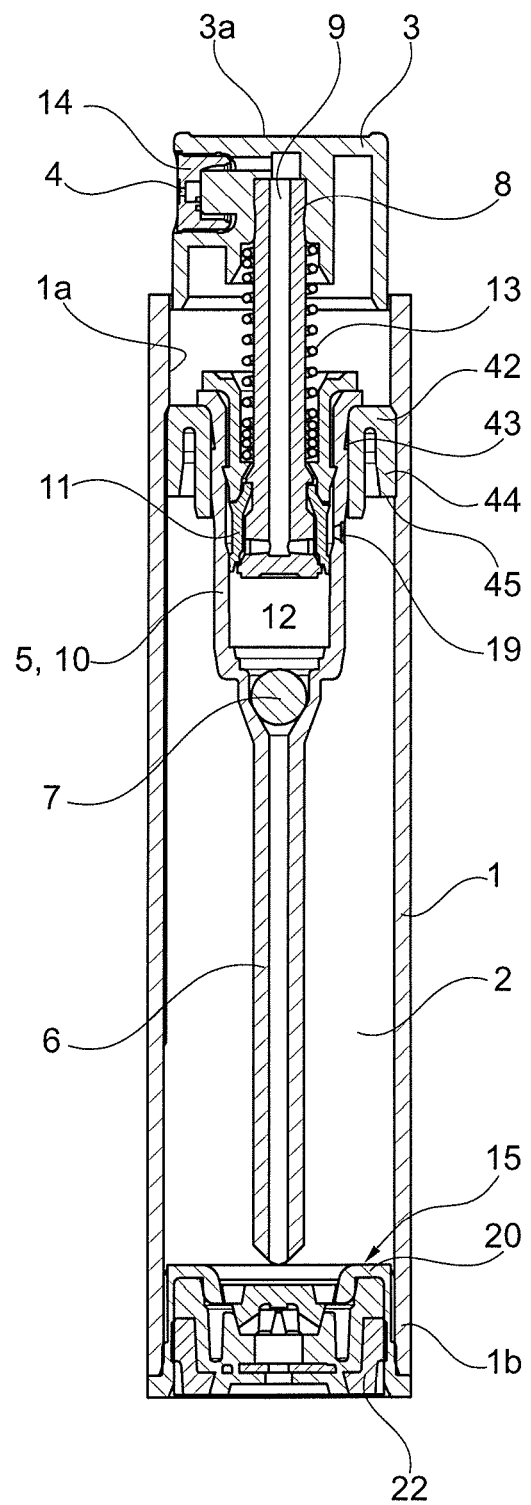
FIG. 3 is a longitudinal cross-section view of the bottle of FIG. 1, which is shown in the use state.

Then, the user can fill the container 2 by suction (FIG. 2), then break the connection means 41 in order to release the pushbutton 3, which is then placed in the resting position, which corresponds to the use state of the bottle (FIG. 3). Alternatively, the connection means 41 can be broken before the container 2 is filled.

In the embodiment shown, the body 1 has an upper opening 1a that is closed by the upper wall 40 and a lower opening 1b in which the cap 20 of the filling valve 15 is mounted in a sealed manner, so as, in particular, to fill the container 2 by the bottom of the bottle, which is an intuitive action.

In addition, the extraction device 5 is mounted in the body 1 by means of a bushing 42, said bushing comprising a bore hole 43 in which the casing 10 is fixed and an exterior crown 44 in sealed contact on the interior of said body. In particular, the extraction device 5 equipped with the bushing 42 is introduced into the lower opening 1b, then translated in the body 1 until the pushbutton 3 is in the depressed position by bearing of the upper area 3a under the upper wall 40.

To ensure the reliability of the pushbutton 3 in the depressed position, the interior of the body 1 has a radial groove 45 on which the exterior crown 44 comes into axial contact at the end of the mounting of the extraction device 5 in said body (FIG. 1C).

In addition, the interior of the body 1 has at least one axial venting groove 46 enabling air to be released during the mounting by sliding of the bushing 42 in the body 1 (FIG. 1B). In addition, to facilitate the air release, the interior of the body 1 can have a conical shape that narrows toward the top.

In the embodiment shown, the body comprises a thinned area 41 that is arranged under the upper wall 40 so as to form the sealed connection means. In particular, the thinned area 41 extends over the entire periphery of the upper opening 1a of the body 1 so as to be capable of separating the upper wall 40 from said body after said area has been destroyed.

In addition, the upper wall 40 is surrounded by a skirt 47, the thinned area 41 of the sealed connection means being formed under said skirt. In relation to the figures, the upper wall 40 and the skirt 47 thus form a cap that, when it is connected to the body 1 by the sealed connection means 41, defines an internal space in which the pushbutton 3 is arranged in the depressed position.

In particular the internal space is in communication with the container 2 since, in the depressed position of the pushbutton 3, the outlet channel 9 of the spray nozzle 8 and therefore the dispensing orifice 4 leading into said internal space is in communication with the container 2 by means of the dosing chamber 14. In addition, the internal space is in communication with the container 2 by means of the vent hole 19.

In addition, to lead the user to grip the skirt 47 in order to destroy the sealed connection means 41, said skirt can have an exterior portion equipped with striations 48, said striations also making it possible to facilitate the gripping of said skirt by said user in order to turn it and/or lift it, so as to break the thinned area 41 in order to release the pushbutton 3.

What is claimed is:

1. A bottle for dispensing a fluid product comprising a body in which a container intended for packaging said product is formed, said bottle also comprising a device for extracting said packaged product, which is mounted in a sealed manner in said body, said extraction device being equipped with a pushbutton that is equipped with an orifice for dispensing said product, said pushbutton being reversibly movable over a stroke for actuation of said device between a resting position and a depressed position in which the dispensing orifice is in communication with the container via said device, said body being equipped with a valve for filling said container that is arranged so as to enable a product source to be placed in communication with said container, the container having an air depression that is arranged so as to be capable of filling the container with product by suction of the product contained in said source, said bottle being characterized in that an upper wall is integrated with the body by way of a sealed connection that can be destroyed manually, said extraction device being mounted in said body with the pushbutton held in the depressed position on said upper wall so as to place said sealed connection in communication with said container.

2. The dispensing bottle according to claim 1, characterized in that the body comprises a thinned area that is arranged under the upper wall so as to form the sealed connection.

3. The dispensing bottle according to claim 1, characterized in that the upper wall is surrounded by a skirt, the sealed connection being formed under said skirt.

4. The dispensing bottle according to claim 3, characterized in that the skirt has an exterior portion equipped with striations.

5. The dispensing bottle according to claim 1, characterized in that the sealed connection extend over the entire periphery of the body so as to be capable of separating the upper wall from said body after destruction of said sealed connection.

6. The dispensing bottle according to claim 1, characterized in that the body has a lower opening in which the filling valve is mounted in a sealed manner.

7. The dispensing bottle according to claim 1, characterized in that the extraction device has a casing that is mounted in the body by means of a bushing, said bushing comprising a bore hole in which said casing is fixed and an exterior crown in sealed contact on the interior of said body.

8. The dispensing bottle according to claim 7, characterized in that the interior of the body has a radial groove on which the exterior crown is in axial abutment.

9. The dispensing bottle according to claim 7, characterized in that the interior of the body has at least on axial groove for venting during the mounting of the bushing in the body.

10. The dispensing bottle according to claim 1, characterized in that the interior of the body has a conical shape that narrows towards the top.

11. The dispensing bottle according to claim 1, characterized in that the valve comprises a rigid cap having an internal housing in which a deformable valve element is mounted, said cap being mounted in a sealed manner in said body so as to place the internal housing in communication with the container by means of a downstream passage.

12. The dispensing bottle according to claim 11, characterized in that the internal housing has a structure equipped with an intermediate passage formed between an upstream opening and a downstream opening, the deformable valve element having a seat equipped with an upstream passage formed between a lower portion for receiving an outlet tube of a product source and an upper portion on which a sealing lip is mounted, said valve being arranged so as to have a stable state in which the sealing lip closes the downstream opening in a sealed manner and a stressed state by axial contact of the outlet tube on the lower portion in which the seat is compressed by axial pressure of the upper portion on the structure enabling communication between the upstream passage and the upstream opening), said compression causing a detachment of said lip so as to open the communication between the downstream opening and the downstream passage so as to enable the container to be filled by sealed communication of the outlet tube with the container by means of passages.

13. The dispensing bottle according to claim 2, characterized in that the upper wall is surrounded by a skirt, said sealed connection being formed under said skirt.

14. The dispensing bottle according to claim 8, characterized in that the interior of the body has at least on axial groove for venting during the mounting of the bushing in the body.

* * * * *